United States Patent [19]

Garnier et al.

[11] 4,369,034
[45] Jan. 18, 1983

[54] DEVICE FOR PREVENTING THE INGRESS OF WATER INTO THE HEAD OF A DENTAL CONTRA-ANGLE

[75] Inventors: Marcel Garnier, Besancon; Michel Seigneurin, St. Cergue, Douvaine, both of France

[73] Assignee: Micro-Mega S.A., France

[21] Appl. No.: 253,649

[22] Filed: Apr. 22, 1981

[30] Foreign Application Priority Data

May 13, 1980 [FR] France .................................. 80 10722
Oct. 10, 1980 [FR] France .................................. 80 21687

[51] Int. Cl.³ ............................................. A61C 1/05
[52] U.S. Cl. .................................................. 433/115
[58] Field of Search ................. 433/115, 116, 132; 277/212 R, 212 F

[56] References Cited

U.S. PATENT DOCUMENTS 2,134,302 10/1938 Hauschalter ........................ 277/212
3,542,372 11/1970 Edwardson ........................ 433/116

*Primary Examiner*—Robert Peshock
*Attorney, Agent, or Firm*—Kane, Dalsimer, Kane, Sullivan and Kurucz

[57] ABSTRACT

This device for preventing the ingress of water into the head of a dental contra-angle comprises a ring seal of cylindrical configuration adapted to be inserted through a hole formed in the bottom wall of the head body for the passage of the dental tool. This ring seal comprises at one end a flange having a diameter greater than the diameter of the passage hole and at its opposite end a bead also of greater diameter than the hole but adapted to be compressed when inserting the ring seal through the hole.

5 Claims, 4 Drawing Figures

DEVICE FOR PREVENTING THE INGRESS OF WATER INTO THE HEAD OF A DENTAL CONTRA-ANGLE

BACKGROUND OF THE INVENTION

This invention relates to dental hand tool holders or handpieces in general and has specific reference to means for preventing the ingress of water into the head of a contra-angle in which the tool clamping chuck is rotatably mounted and driven, the head end adjacent the tool being closed by a wall formed with a hole permitting the passage of said tool.

When a drill cuts a cavity in a tooth, the working end of the tool is sprinkled by directing an air and water mist, or only water, thereagainst. In this case the water spray hits very irregular surfaces and rebounds in all directions, including along the drill shank, from which it is liable to penetrate into the contra-angle head.

THE PRIOR ART

The conventional method of ejecting this undesired water consist in providing a ring seal either fixed to the drill shank or simply retained by frictional engagement thereon. Thus, any water rising on the peripheral surface of the ring seal is ejected by the centrifugal force.

Now, not all drills are provided with this ring seal and the mere fact of fitting a split ring when inserting a drill into the contra-angle constitutes a tedious and sometimes difficult operation.

SUMMARY OF THE INVENTION

It is the primary object of the present invention to avoid the inconveniences set forth hereinabove by providing an improved device characterized in that it comprises a cylindrical or ring seal, grommet or sleeve having a central bore matching the tool diameter; this ring seal is disposed inside the contra-angle head, coaxially to the chuck, in the space available between said end wall and the chuck outer end, and extends with a moderate clearance through the hole formed in said wall for the passage of the drill or other tool; furthermore, the ring seal is retained in said space by an integral flange having a greater diameter than said orifice.

Thus, any water tending to splash up against the drill and penetrate into the head inner space left between the drill and the passage hole formed through the adjacent head end wall will be stopped and then ejected due to the rotation of the drill-driven ring seal.

In a preferred form of embodiment of the present invention the ring seal comprises at its lower end projecting from the head end wall an integral annular bead having an outer diameter slightly greater than the hole diameter, for retaining the ring seal in said hole.

Consequently, when the practitioner removes the head from the handpiece, the ring seal remains in position in the hole due to the complementary presence of its flange and bead disposed on either side of the wall through which the hole is formed. If desired, the ring seal may be removed from this hole by driving the bead through it.

THE DRAWINGS

DESCRIPTION OF THE PREFERRED EMBODIMENTS

Figure 1:
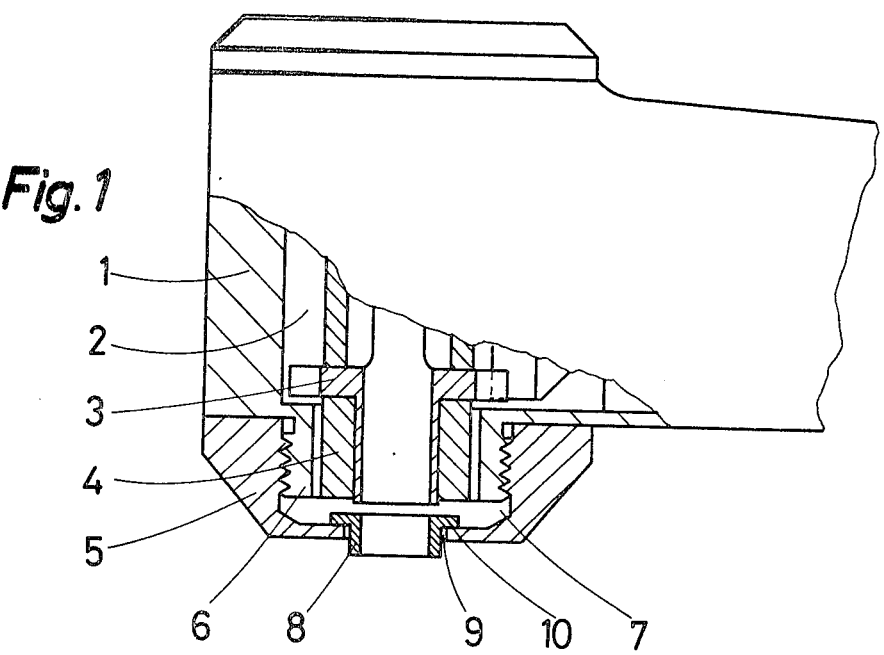
FIG. 1 is a diagrammatic, part-sectional view showing the outer end of a contra-angle head provided with the ring seal of this invention but without the drill.

Referring first to FIG. 1, the dental contra-angle head comprises a head body 1 in which a cylindrical bore 2 is formed for receiving the tool clamping chuck 3, this tool consisting for example of a drill (not shown). The chuck 3 in which the drill shank is retained by frictional contact revolves in a bearing 4 force-fitted in turn in the head body 1. A screw-plug 5 is engaged in the tapped end of body 1 and its axial length is such that a space 7 is left between the bottom face of this plug 5 and the outer end of the clamping chuck 3 which protrudes slightly from the end 6 of head body 1.

A split ring seal, sleeve or grommet 8 having a bore diameter consistent with the diameter of the drill shank and in axial alignment with the chuck extends with a small clearance through the hole 9 formed in the bottom of plug 5 for engagement by the drill shank. This ring seal 8 is retained in said space 7 by a flange 10 formed integrally with the ring seal; the outer diameter of flange 10 is greater than the diameter of hole 9.

When the drill is introduced into the contra-angle, it is forced through the ring seal 8 so as to press the latter against the outer end of chuck 3; therefore, the rear end of the shank will pass through the ring seal 8 and eventually engage the chuck 3 in which it is retained by frictional contact. Under these conditions the ring seal 8 is rotatably driven by the drill shank due to its frictional contact therewith, and since it was previously pressed by the drill against the chuck 3, it will not contact the plug 5. The clearance between the ring seal 8 and the wall of hole 9 in plug 5 is slightly in excess of the clearance provided between the chuck 3 and its bearing 4.

Figure 2:
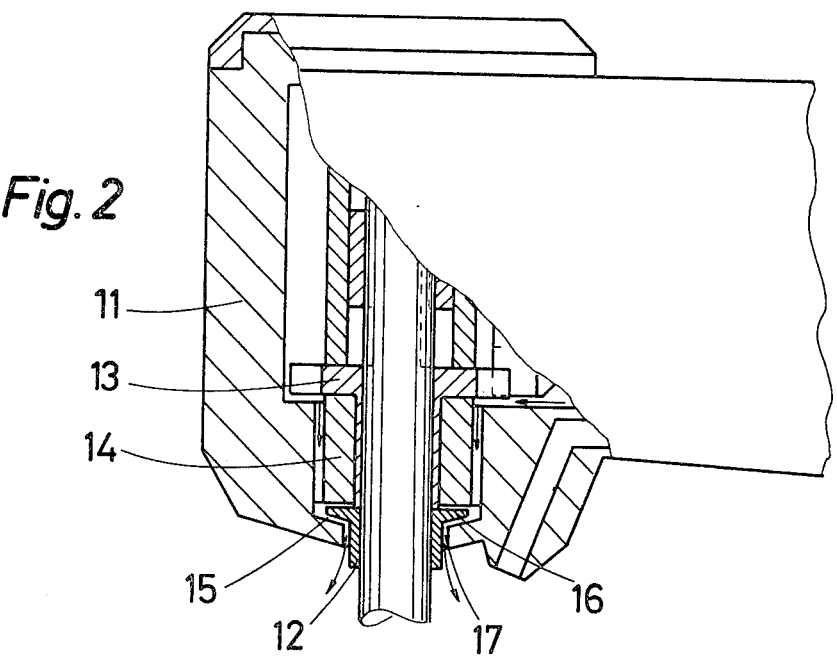
FIG. 2 is a view similar to FIG. 1 but showin the fitting of the ring seal of this invention to a different head configuration, with the drill shank inserted therethrough.

In a modified form of embodiment of the contra-angle head shown in FIG. 2, the head body 11 is formed integrally with the plug and the ring seal 12 is fitted in the bottom portion of the head body 11 before assembling the other component elements, i.e. the chuck 13 and its bearing 14. The relative arrangement of the component elements is such that, as in the preceding form of embodiment shown in FIG. 1, a space 15 is left between the bottom of the head body 11 and the chuck 13 for receiving the flange 16 of ring seal 12. As in the preceding form of embodiment, the ring seal 12 extends with a small clearance through the hole 17 provided for the passage of the drill shank 18, and the diameter of the ring seal bore is consistent with the diameter of said shank so as to be retained thereby by frictional engagement.

Figure 3:
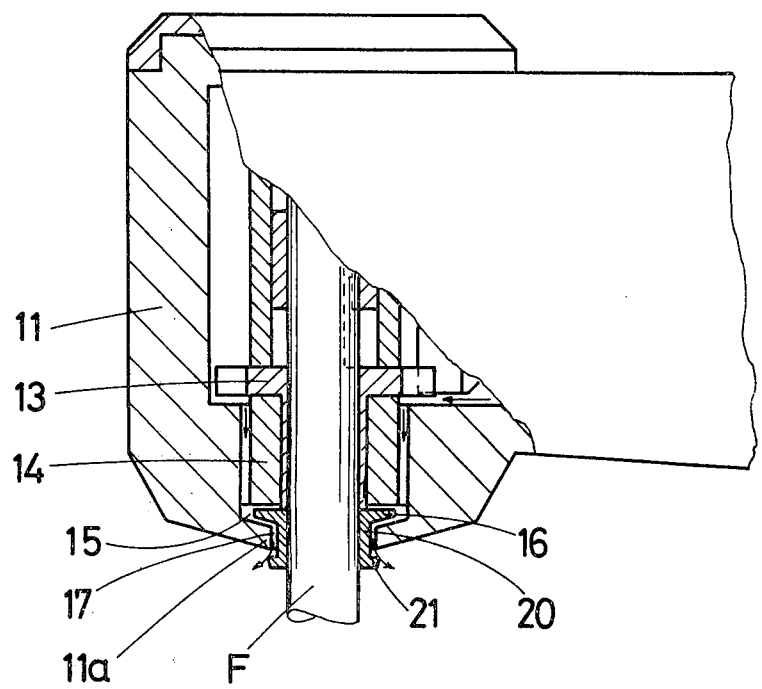
FIG. 3 is another diagrammatic, part-sectional view of a modified form of embodiment of the ring seal fitted to a contra-angle head similar to that shown in FIG. 2.

In another modified form of embodiment shown in FIG. 3, the contra-angle head as in the preceding example is a one-piece structure 11 and the ring seal 20 is fitted in the hole 17 formed through the bottom wall 11a of the head body 11 before assembling the other component elements, i.e. the chuck 13 and its bearing 14. The upper end of ring seal 20, as seen in the Figure, comprises an integral flange 16 and a complementary integral bead 21 is formed at its lower end, as shown. The diameters of flange 16 and bead 21 are slightly greater than that of hole 17, and the diameter of the ring seal portion 20 extending between said flange 16 and bead 21 is slightly smaller than the diameter of said hole 17 in order to provide a clearance permitting the passage of air. Furthermore, the bore of ring seal 20 is consistent with the diameter of the drill shank, so that when the latter is driven axially therethrough the frictional contact between the ring seal and the shank enables the latter to rotatably drive the former.

Figure 4:
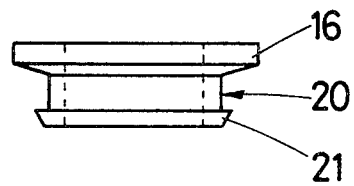
FIG. 4 is a side elevational view of the ring seal alone.

As clearly shown in FIG. 4, the diameter of bead 21 is preferably slightly smaller than that of flange 16 in order to facilitate the fitting of the ring seal 20 through the hole 17.

The ring seal 20 may be made from any suitable plastic elastomeric material capable of withstanding temperatures of the order of 180° C., notably a material such as TEFLON, a Registered Trade Mark, whereby the ring seal can be driven through the hole 17 by simply pushing the ring seal, so that the bead 21 will firstly be contracted to penetrate this hole and then be allowed to expand and resume its original shape beyond the bottom 11a (FIG. 3). When the drill F is introduced into the clamping chuck 13, it carries along by friction the ring seal 20 while the flange 16 moves within the space 15 formed between the bottom 11a and the bearing 14.

If desired, the ring seal may be split to facilitate the fitting thereof into the hole 17.

What is claimed is:

1. A device for preventing the ingress of water into the head of a dental contra-angle in which the tool clamping chuck is rotatably driven, the head end on the tool side being closed by a wall in which a hole is formed to permit the passage of the tool, wherein the device comprises a cylindrical ring seal having a bore consistent with the tool shank diameter, said ring seal being adapted to turn with the shank and to be fitted within said head in axial alignment with said chuck, in the space left between said end wall and the outer end of said chuck, said ring seal extending with a relatively small clearance through said tool passage hole and being retained in said space by an integral flange having a greater diameter than said hole.

2. The device of claim 1, wherein said clearance between said ring seal and said tool passage hole is greater than the clearance between said chuck and the chuck bearing.

3. The device of claim 2, wherein said ring seal further comprises at its end projecting from said end wall an annular bead having a diameter greater than that of said hole, for retaining in conjunction with said flange said ring seal in said hole.

4. The device of claim 3, wherein said ring seal is made from a suitable elastomeric material.

5. The device of claim 4, wherein said ring seal is split.

* * * * *